United States Patent [19]

Tomcufcik et al.

[11] Patent Number: 4,980,472

[45] Date of Patent: Dec. 25, 1990

[54] METHOD OF MAKING (3-AMINO-1H-PYRAZOL-4-YL) (ARYL)METHANONES

[75] Inventors: Andrew S. Tomcufcik, Old Tappan, N.J.; John P. Dusza, Nanuet, N.Y.

[73] Assignee: American Cyanamid Company, Stamford, Conn.

[21] Appl. No.: 437,280

[22] Filed: Nov. 15, 1989

Related U.S. Application Data

[60] Division of Ser. No. 612,811, May 24, 1984, Pat. No. 4,900,836, which is a continuation-in-part of Ser. No. 507,317, Jun. 23, 1983, abandoned.

[51] Int. Cl.$^5$ .................. C07D 401/06; C07D 405/06
[52] U.S. Cl. .................... 544/405; 546/279; 548/362; 548/374; 548/375; 548/377
[58] Field of Search ............ 544/405; 546/279; 548/362, 374, 375, 377

[56] References Cited

U.S. PATENT DOCUMENTS 3,660,425  5/1972  DeWald et al. .............. 548/362

FOREIGN PATENT DOCUMENTS 10508  3/1974  Japan ............................. 548/362

OTHER PUBLICATIONS

Butler and DeWald, "New General Methods . . . ", J. Org. Chem., 1971, 36, pp. 2542–2547.
Butler, Wise and DeWald, "(1,3-Dialkyl-5-amino-1-H-pyrazol-4-yl)aryl-methanones", J. Med. Chem., 1984, 27, pp. 1346–1400.

*Primary Examiner*—Mary C. Lee
*Assistant Examiner*—Catherine Scalzo
*Attorney, Agent, or Firm*—H. G. Jackson

[57] ABSTRACT

(3-Amino-1H-pyrazol-4-yl)(aryl)methanones which are new compounds having utility as intermediates for the preparation of aryl and heteroaryl-[7-(aryl and heteroaryl)pyrazolo[1,5-a]pyrimidin-3-yl]methanones, which are therapeutic agents.

7 Claims, No Drawings

METHOD OF MAKING (3-AMINO-1H-PYRAZOL-4-YL) (ARYL)METHANONES

CROSS REFERENCE TO RELATED APPLICATION

This is a divisional of application Ser. No. 06/612,811 filed May 24, 1984, now U.S. Pat. No. 4,900,836, which is in turn a continuation-in-part of application Ser. No. 06/507,317, filed on June 23, 1983, which has been abandoned.

SUMMARY OF THE INVENTION

This invention relates to new organic compounds which may be represented by the following structural formula:

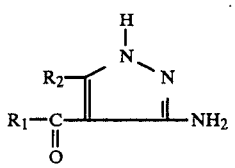

wherein $R_1$ is selected from the group consisting of Phenyl; phenyl substituted by one or two of the group selected from halogen, alkyl ($C_1$–$C_3$) and alkoxy($C_1$–$C_3$); Phenyl tribsubstituted by methoxy phenyl substituted by one of the group consisting of dialkylamino($C_1$–$C_3$), methylenedioxy, alkylthio($C_1$–$C_3$), alkylsulfonyl($C_1$–$C_3$), trifluoromethyl and phenyl; pyridinyl; pyridinyl substituted by one or two of the group selected from halogen, alkyl($C_1$–$C_3$) and alkoxy($C_1$–$C_3$); thienyl; thienyl substituted by one or two of the group selected from halogen, alkyl($C_1$–$C_3$) and alkoxy($C_1$–$C_3$); furanyl; naphthalenyl; and pyrazinyl; and $R_2$ is selected from the group consisting of hydrogen and alkyl($C_1$–$C_3$).

DETAILED DESCRIPTION OF THE INVENTION

The compounds of the present invention may be readily prepared as set forth in the following reaction scheme:

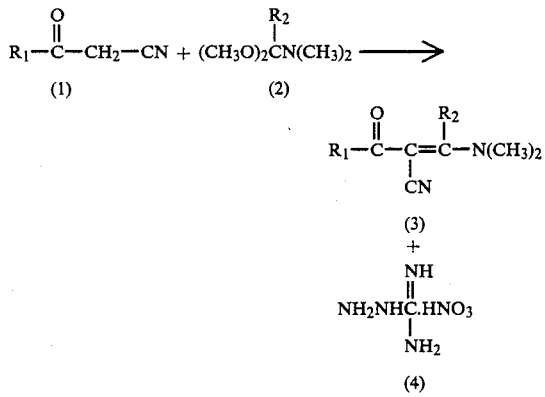

In accordance with the above reaction scheme an appropriately substituted acetonitrile (1), where $R_1$ is as described above is reacted with a dimethylamide dimethylacetal (2) where $R_2$ is as described above. The resulting exothermic reaction produces a crystalline solid which is recovered by evaporation and dissolved in methylene chloride. This solution is passed through hydrous magnesium silicate and hexane is added to the refluxing eluate, giving the [($\alpha$-dimethylamino)methylene]-$\beta$-oxoarylpropanenitrile (3) which is then reacted with aminoguanidine nitrate (4) in the presence of 10N sodium hydroxide and a lower alkanol at reflux for several hours then evaporated to dryness and crystallized from water, ethanol or other suitable solvent, giving (5). The aminoguanidine nitrate may be replaced by other salts of aminoguanidine, such as the hydrochloride, sulfate, and the like. Alternatively, the aminoguanidine salt-sodium hydroxide combination may be replaced by an equivalent of aminoguanidine bicarbonate or thiosemicarbazide, both reagents resulting in the formation of (5).

The (3-amino-1H-pyrazol-4-yl)(aryl)methanones find utility as intermediates in the preparation of therapeutic aryl and heteroaryl[7-(aryl and heteroaryl)pyrazolo[1,5-a]pyrimidin-3-yl]methanones which are useful as anxiolytic or antiepileptic agents as well as sedative-hypnotic and skeletal muscle relaxant agents.

These aryl and heteroaryl(7-(aryl and heteroaryl)-pyrazolo(1,5-a)-pyrimidin-3-yl)methanones have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds are preferably administered orally but may be administered in any convenient manner such as by the intravenous, intramuscular, or subcutaneous routes.

The novel compounds of this invention may be readily used to prepare these aryl and heteroaryl(7-(aryl and heteroaryl)-pyrazolo(1,5-a)pyriminidin-3-yl)methanones as set forth in the following scheme:

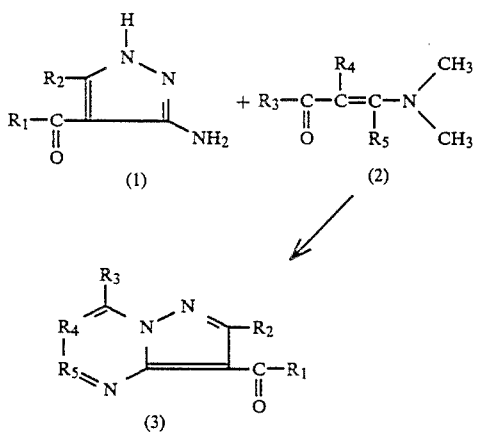

The reaction of an appropriately substituted pyrazole (1) and an appropriately substituted 3-dimethylamino-1-(aryl or heteroaryl)-2-propen-1-one (2) in glacial acetic acid at reflux temperature for several hours, followed by solvent removal partitioning of the residue between saturated aqueous sodium bicarbonate and methylene chloride, passage of the organic layer through hydrous magnesium silicate and the addition of hexane to the refluxing eluate produces the desired products (3).

The substituted 3-dimethylamino-1-(aryl) or (heteroaryl)-2-propen-1-ones (2) are disclosed in one or more of U.S. Pat. Nos. 4,178,449; 4,281,000; and 4,236,005.

Pyrazolo(1,5-a)pyrimidines are prepared by condensation of 3-aminopyrazoles and substituted 3-aminopyrazoles with 1,3-dicarbonyl compounds as described in J. Med. Chem., 18, 645 (1974); J. Med. Chem., 460 (1975); J. Med. Chem., 20, 386 (1977); Synthesis, 673 (1982) and references contained therein.

7-aryl and 7-heteroaryl(1,5-a)pyrimidines, which contain a 3-aroyl group, are synthesized by condensation of 1-aryl or 1-heteroaryl-1,3-dicarbonyl compounds with 3-amino-4-aroylpyrazoles.

The following non-limiting examples illustrate the preparation of the compounds of the present invention.

EXAMPLE 1

α-[(Dimethylamino)methylene]-β-oxo-2-furanepropanenitrile

A 50 ml portion of dimethylformamide dimethylacetal was added to 25 g of solid β-oxo-2-furanepropanenitrile. This exothermic reaction produced yellow crystals. After one hour the volatiles were removed under reduced pressure and the residue was dissolved in methylene chloride. This solution was passed through a short pad of hydrous magnesium silicate. The eluate was refluxed with the gradual addition of hexane to the point of turbidity. Cooling and filtration gave 35.2 g of the desired compound, mp 117°–125° C.

EXAMPLE 2

α-[(Dimethylamino)methylene]-β-oxo-benzenepropanenitrile

A 100 g portion of β-oxo-benzenepropanenitrile was placed in a 500 ml round-bottom flask and 110 ml of dimethylformamide dimethylacetal was added in one portion. The reaction mixture became warm and a homogeneous dark yellow solution resulted, which then solidified. After cooling to room temperature, hexane was added giving crystals which were recovered by filtration. This material (143.6 g, mp 102°–105° C.) is suitable for the subsequent reaction without further purification.

An analytical sample of this compound was obtained by dissolution in methylene chloride followed by passage through a short column of hydrous magnesium silicate, concentration of the eluate with the gradual addition of hexane until crystallization occurred, cooling and collection by filtration, mp 111°–113° C.

Following the general procedures of Examples 1 or 2, the following compounds of Examples 3–31, shown in Table I were prepared.

TABLE I

| Example | Acetonitrile | Compound | MP°C. |
|---|---|---|---|
| 3 | β-oxo-4-fluorobenzenepropanenitrile | α-[(dimethylamino)methylene]-β-oxo-4-fluorobenzenepropanenitrile | 142–145 |
| 4 | β-oxo-(3-trifluoromethyl)benzenepropanenitrile | α-[(dimethylamino)methylene]-β-oxo-3-(trifluoromethyl)benzenepropanenitrile | 93–96 |
| 5 | β-oxo-4-pyridinepropanenitrile | α-[(dimethylamino)methylene]-β-oxo-4-pyridinepropanenitrile | 127–128 |
| 6 | β-oxo-2-thiophenepropanenitrile | α-[(dimethylamino)methylene]-β-oxo-2-thiophenepropanenitrile | 136–140 |
| 7 | β-oxo-4-methylbenzenepropanenitrile | α-[(dimethylamino)methylene]-β-oxo-4-methylbenzenepropanenitrile | 132–135 |
| 8 | β-oxo-2-pyridinepropanenitrile | α-[(dimethylamino)methylene]-β-oxo-2-pyridinepropanenitrile | 88–90 |
| 9 | β-oxo-3-fluorophenylpropanenitrile | α-[(dimethylamino)methylene]-β-oxo-3-fluorophenylpropanenitrile | 63–68 |
| 10 | β-oxo-2-chlorophenylpropanenitrile | α-[(dimethylamino)methylene]-β-oxo-2-chlorophenylpropanenitrile | 152–154 |
| 11 | β-oxo-3-furanylpropanenitrile | α-[(dimethylamino)methylene]-β-oxo-3-furanylpropanenitrile | 98–103 |
| 12 | β-oxo-3,4,5-trimethoxyphenylpropanenitrile | α-[(dimethylamino)methylene]-β-oxo-3,4,5-trimethoxyphenylpropanenitrile | 138–140 |
| 13 | β-oxo-3,4-dimethoxyphenylpropanenitrile | α-[(dimethylamino)methylene]-β-oxo-3,4-dimethoxyphenylpropanenitrile | glassy solid |
| 14 | β-oxo-3-methylphenylpropanenitrile | α-[(dimethylamino)methylene]-β-oxo-3-methylphenylpropanenitrile | 74–80 |
| 15 | β-oxo-3,5-dimethoxyphenylpropanenitrile | α-[(dimethylamino)methylene]-β-oxo-3,5-dimethoxyphenylpropanenitrile | 125–127 |
| 16 | β-oxo-4-chlorophenylpropanenitrile | α-[(dimethylamino)methylene]-β-oxo-4-chlorophenylpropanenitrile | 118–121 |
| 17 | β-oxo-4-methoxyphenylpropane- | α-[(dimethylamino)methylene]-β-oxo-4- | 128–130 |

TABLE I-continued

| Example | Acetonitrile | Compound | MP°C. |
|---|---|---|---|
| | nitrile | methoxyphenylpropanenitrile | |
| 18 | β-oxo-2-fluorophenylpropanenitrile | α-[(dimethylamino)methylene]-β-oxo-2-fluorophenylpropanenitrile | 62–74 |
| 19 | β-oxo-3-methoxyphenylpropanenitrile | α-[(dimethylamino)methylene]-β-oxo-3-methoxypnehylpropanenitrile | Syrup |
| 20 | β-oxo-[4-(trifluoromethyl)-phenyl]propanenitrile | α-[(dimethylamino)methylene]-β-oxo-[4-(trifluoromethyl)phenyl]propanenitrile | 122–123 |
| 21 | β-oxo-3-chlorophenylpropanenitrile | α-[(dimethylamino)methylene]-β-oxo-3-chlorophenylpropanenitrile | Syrup |
| 22 | β-oxo-2,5-dichlorophenylpropanenitrile | α-[(dimethylamino)methylene]-β-oxo-2,5-dichlorophenylpropanenitrile | 140–143 |
| 23 | β-oxo-2-methylphenylpropanenitrile | α-[(dimethylamino)methylene]-β-oxo-2-methylpenylpropanenitrile | 82–84 |
| 24 | β-oxo-[4-(dimethylamino)phenyl]propanenitrile | α-[(dimethylamino)methylene]-β-oxo-[4-(dimethylamino)phenyl]propanenitrile | 208–210 |
| 25 | β-oxo-2-methoxyphenylpropanenitrile | α-[(dimethylamino)methylene]-β-oxo-2-methoxyphenylpropanenitrile | 105–115 |
| 26 | β-oxo-[3,4-(methylenedioxy)phenyl]propanenitrile | α-[(dimethylamino)methylene]-β-oxo-[3,4-(methylenedioxy)phenyl]propanenitrile | 118–124 |
| 27 | β-oxo-4-ethoxyphenylpropanenitrile | α-[(dimethylamino)methylene]-β-oxo-4-ethoxyphenylpropanenitrile | 110–115 |
| 28 | β-oxo-4-ethylphenylpropanenitrile | α-[(dimethylamino)methylene]-β-oxo-4-ethyphenylpropanenitrile | 48–54 |
| 29 | β-oxo-2-naphthalenylpropanenitrile | α-[(dimethylamino)methylene]-β-oxo-2-naphthalenylpropanenitrile | 115–118 |
| 30 | β-oxo-5-methyl-2-thienylpropanenitrile | α-[(dimethylamino)methylene]-β-oxo-5-methyl-2-thienylpropanenitrile | 152–153 |
| 31 | β-oxo-2-thienylpropanenitrile | α-[(dimethylamino)methylene]-β-oxo-2-thienylpropanenitrile | 118–120 |

EXAMPLE 32

α-](1-Dimethylamino)ethylidene]-β-oxo-phenyl-propanenitrile

A solution of 14.5 grams of benzoylacetonitrile in 100 ml of chloroform was cooled to −10° C. and stirred as a solution of 13.3 g of N,N-dimethylacetamide dimethylacetal in 20 ml of chloroform was added dropwise during 15 minutes. The reaction temperature was not allowed to exceed −5° C. Stirring was continued at −5° to −10° C. for two hours after addition ended. The resultant reaction mixture was dissolved in 150 ml of benzene and the solution passed through a layer of hydrous magnesium silicate. Evaporation of the filtrate in air left a yellow residue which was purified by recrystallization from a mixture of benzene and low boiling petroleum ether; yield, 5.8 g, mp 105°–106° C.

EXAMPLE 33

(3-Amino-1H-pyrazol-4-yl)(2-furanyl)methanone

A reaction mixture comprising 19.0 g of α-[(dimethylamino)methylene]-β-oxo-2-furanepropanenitrile, 16.1 g of aminoguanidine nitrate, 250 ml of ethanol and 11.0 ml of 10N sodium hydroxide was refluxed for 6 hours and then evaporated to dryness. Water was added to the crude residue and the precipitated solid was collected, giving 17.0 g of the desired product, mp 153°–155° C.

EXAMPLE 34

(3-Amino-1H-pyrazol-4-yl) phenylmethanone

A reaction mixture comprising 73.36 g of α-(dimethylamino)methylene]-β-oxo-2-benzenepropanenitrile, 63.45 g of aminoguanidine nitrate, 500 ml of ethanol and 36.6 ml of 10N sodium hydroxide was refluxed for 10 hours and then cooled. The resulting precipitate was collected and washed with water, giving 17.1 g of the desired product, mp 177°–179° C.

When the aminoguanidine nitrate-10N sodium hydroxide combination was replaced by an equivalent of aminoguanidine bicarbonate, the identical product was obtained as shown by its melting point, elemental analysis and infrared and nuclear magnetic resonance absorption spectra. A similar result was obtained when an equivalent of thiosemicarbazide replaced the aminoguanidine nitrate10N sodium hydroxide combination.

Following the general procedures of Examples 33 and 34. employing the compounds of Examples 1–32 and the appropriate guanidine derivatives, the products of Examples 35–64, given in Table II, were prepared.

TABLE II

| Example | Starting Material of Example | Product | MP °C. |
|---|---|---|---|
| 35 | 3 | (3-amino-1H-pyrazol-4-yl)(4-fluorophenyl)methanone | 172–175 |
| 36 | 4 | (3-amino-1H-pyrazol-4-yl)[3-(trifluoromethyl)phenyl]methanone | 134–136 |
| 37 | 5 | (3-amino-1H-pyrazol-4-yl)(4-pyridinyl)methanone | 275–277 |
| 38 | 6 | (3-amino-1H-pyrazol-4-yl)(2-thienyl)methanone | 144–145 |
| 39 | 32 | (3-amino-5-methyl-1H-pyrazol-4-yl) phenylmethanone | 179–180 |
| 40 | 7 | (3-amino-1H-pyrazol-4-yl)(4-pyridinyl)methanone | 118–120 |
| 41 | 8 | (3-amino-1H-pyrazol-4-yl)(2-pyridinyl)methanone | 177–179 |
| 42 | 9 | (3-amino-1H-pyrazol-4-yl)(3-fluorophenyl)methanone | 188–189 |
| 43 | 10 | (3-amino-1H-pyrazol-4-yl)(2-chlorophenyl)methanone | glassy solid |
| 44 | 11 | (3-amino-1H-pyrazol-4-yl)(3-furanyl)methanone | 211–215 |
| 45 | 12 | (3-amino-1H-pyrazol-4-yl)(3,4,5-trimethoxyphenyl)methanone | 199–201 |
| 46 | 13 | (3-amino-1H-pyrazol-4-yl)(3,4-dimethoxyphenyl)methanone | 108–109 |
| 47 | 14 | (3-amino-1H-pyrazol-4-yl)(3-methylphenyl)methanone | 137–139 |
| 48 | 15 | (3-amino-1H-pyrazol-4-yl)(3,5-dimethoxyphenyl)methanone | 91–92 |
| 49 | 16 | (3-amino-1H-pyrazol-4-yl)(4-chlorophenyl)methanone | 235–237 |
| 50 | 17 | (3-amino-1H-pyrazol-4-yl)(4-Methoxyphenyl)methanone | 172–174 |
| 51 | 18 | (3-amino-1H-pyrazol-4-yl)(2-fluorophenyl)methanone | glassy solid |
| 52 | 19 | (3-amino-1H-pyrazol-4-yl)-(3-methoxyphenyl)methanone | 96–98 |
| 53 | 20 | (3-amino-1H-pyrazol-4-yl)-[4-(trifluoromethyl)phenyl)methanone | 172–174 |
| 54 | 21 | (3-amino-1H-pyrazol-4-yl)-(3-chlorophenyl)methanone | 229–230 |
| 55 | 22 | (3-amino-1H-pyrazol-4-yl-(2,5-dichlorophenyl)methanone | Syrup |
| 56 | 23 | (3-amino-1H-pyrazol-4-yl)-(2-methylphenyl)methanone | Glass |
| 57 | 24 | (3-amino-1H-pyrazol-4-yl)-[4-(dimethylamino)phenyl]-methanone | 240–243 |
| 58 | 25 | (3-amino-1H-pyrazol-4-yl)-(2-methoxyphenyl)methanone | Glass |
| 59 | 26 | (3-amino-1H-pyrazol-4-yl)-[3,4-(methylenedioxy)phenyl]methanone | 228–230 |
| 60 | 27 | (3-amino-1H-pyrazol-4-yl)-(4-ethoxyphenyl)methanone | 155–156 |
| 61 | 28 | (3-amino-1H-pyrazol-4-yl)-(4-ethylphenyl)methanone | 108–109 |
| 62 | 29 | (3-amino-1H-pyrazol-4-yl)-(2-naphthalenyl)methanone | 215–217 |
| 63 | 30 | (3-amino-1H-pyrazol-4-yl)-(5-methyl-2-thienyl)methanone | 165–166 |
| 64 | 31 | (3-amino-1H-pyrazol-4-yl)-(2-thienyl)methanone | 181–183 |

What is claimed is:

1. A process for the preparation of a compound of the formula:

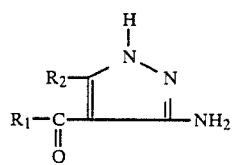

wherein $R_1$ is selected from the group consisting of phenyl substituted by one or two of the group selected from halogen, alkyl($C_1$-$C_3$) and alkoxy($C_1$-$C_3$); phenyl trisubstituted by methoxy; phenyl substituted by one of the group consisting of dialkylamino($C_1$-$C_3$), methylenedioxy, alkylthio($C_1$-$C_3$), alkylsulfonyl($C_1$-$C_3$), amino, alkanoyl($C_1$-$C_3$)amino, trifluoromethyl and phenyl; pyridinyl; pyridinyl substituted by one or two of the group selected from halogen, alkyl($C_1$-$C_3$) and alkoxy($C_1$-$C_3$); thienyl; thienyl substituted by one or two of the group selected from halogen, alkyl($C_1$-$C_3$) and alkoxy($C_1$-$C_3$); furanyl; naphthalenyl; and pyrazinyl; and $R_2$ is selected from the group consisting of hydrogen and alkyl($C_1$-$C_3$);

which comprises:

condensing a first compound of the formula

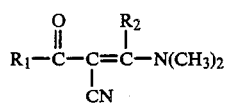

wherein $R_1$ and $R_2$ are as defined above;

with a second compound of the formula

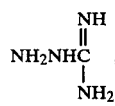

or a salt or a derivative thereof.

2. A process as defined in claim 1 which includes the step of producing said first compound by reacting a compound of the formula:

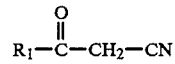

wherein $R_1$ is selected from the group consisting of phenyl substituted by one or two of the group selected from halogen, alkyl($C_1$-$C_3$) and alkoxy($C_1$-$C_3$); phenyl trisubstituted by methoxy; phenyl substituted by one of the group consisting of dialkylamino($C_1$-$C_3$), methylenedioxy, alkylthio ($C_1$-$C_3$), alkylsulfonyl ($C_1$-$C_3$), amino, alkanoyl($C_1$-$C_3$)amino, trifluoromethyl and phenyl; pyridinyl; pyridinyl substituted by one or two of the group selected from halogen, alkyl($C_1$-$C_3$) and alkoxy($C_1$-$C_3$); thienyl; thienyl substituted by one or two of the group selected from halogen, alkyl($C_1$-$C_3$) and alkoxy($C_1$-$C_3$); furanyl; naphthalenyl; and pyrazinyl; with a compound of the formula:

wherein $R_2$ is selected from the group consisting of hydrogen and alkyl($C_1$-$C_3$).

3. A process as defined in claim 1 wherein (3-amino-1H-pyrazol-4-yl)(2-furanyl)methanone is produced.

4. A process as defined in claim 1 wherein (3-amino-1H-pyrazol-4-yl)(4-pyridinyl)methanone is produced.

5. A process as defined in claim 1 wherein (3-amino-1H-pyrazol-4-yl)(2-thienyl)methanone is produced.

6. A process as defined in claim 1 wherein (3-amino-1H-pyrazol-4-yl)(2-pyridinyl)methanone is produced.

7. A process as defined in claim 1 wherein (3-amino-1H-pyrazol-4-yl)(3-furanyl)methanone is produced.

* * * * *